United States Patent
Menninger

(10) Patent No.: US 6,676,621 B1
(45) Date of Patent: Jan. 13, 2004

(54) BLOOD TREATMENT MACHINE

(75) Inventor: Stefan Menninger, Würzburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/429,422

(22) Filed: Oct. 28, 1999

(30) Foreign Application Priority Data

Oct. 28, 1998 (DE) .......................................... 198 49 787

(51) Int. Cl.⁷ ....................... A61M 37/00; A61M 31/00; A61M 1/34; C02F 1/44
(52) U.S. Cl. ....................... 604/4.01; 604/6.09; 604/67; 422/44; 210/645
(58) Field of Search ................................. 604/4.01, 6.01, 604/65, 67; 422/44–48; 210/645, 646; 706/52, 55, 924; 714/25, 819, 822

(56) References Cited

U.S. PATENT DOCUMENTS

| | | | |
|---|---|---|---|
| 4,298,982 A | * 11/1981 | Auerbach .................... | 714/735 |
| 4,358,823 A | * 11/1982 | McDonald et al. ........... | 714/11 |
| 5,345,566 A | * 9/1994 | Tanji et al. .................. | 710/306 |
| 5,696,895 A | * 12/1997 | Hemphill et al. ............. | 714/13 |
| 5,784,547 A | * 7/1998 | Dittmar et al. ............... | 714/4 |
| 5,910,252 A | * 6/1999 | Truitt et al. .................. | 210/103 |
| 6,139,754 A | * 10/2000 | Hartranft et al. ............ | 210/101 |
| 6,334,194 B1 | * 12/2001 | Hihara ........................ | 712/32 |

FOREIGN PATENT DOCUMENTS

| | | |
|---|---|---|
| DE | 37 36 712 | 5/1988 |
| DE | 41 36 338 | 5/1993 |
| DE | 44 16 795 | 11/1995 |
| EP | 0 384 155 | 8/1990 |

OTHER PUBLICATIONS

Service Manual—Trio CVVH–System.
Daniel P. Siewiorek, Architecture of Fault–Tolerant Computers: An Historical Perspective, Proceedings of the IEEE, vol. 79, No. 12, Dec. 1991, pp. 1710–1734.

* cited by examiner

Primary Examiner—Angela D. Sykes
Assistant Examiner—Leslie R. Deak
(74) Attorney, Agent, or Firm—Kenyon & Kenyon

(57) ABSTRACT

A blood treatment machine to further increase the functional reliability of blood purifying machines having a blood treatment component, including a blood line for transport of blood between a patient and the blood treatment component, several control units for monitoring and controlling the blood transport and/or the blood treatment, and at least two control units each comprising an action computer and an auxiliary computer. The action computers are interconnected via an action bus, and the auxiliary computers are interconnected via an auxiliary bus. A table is stored wherein error cases occurring on the respective control unit and/or error messages received by the respective control unit are assigned to an error processing routine, and the action computer and/or the auxiliary computer of a control unit places an error message on the respective bus as soon as an error occurs on the respective control unit.

9 Claims, 2 Drawing Sheets

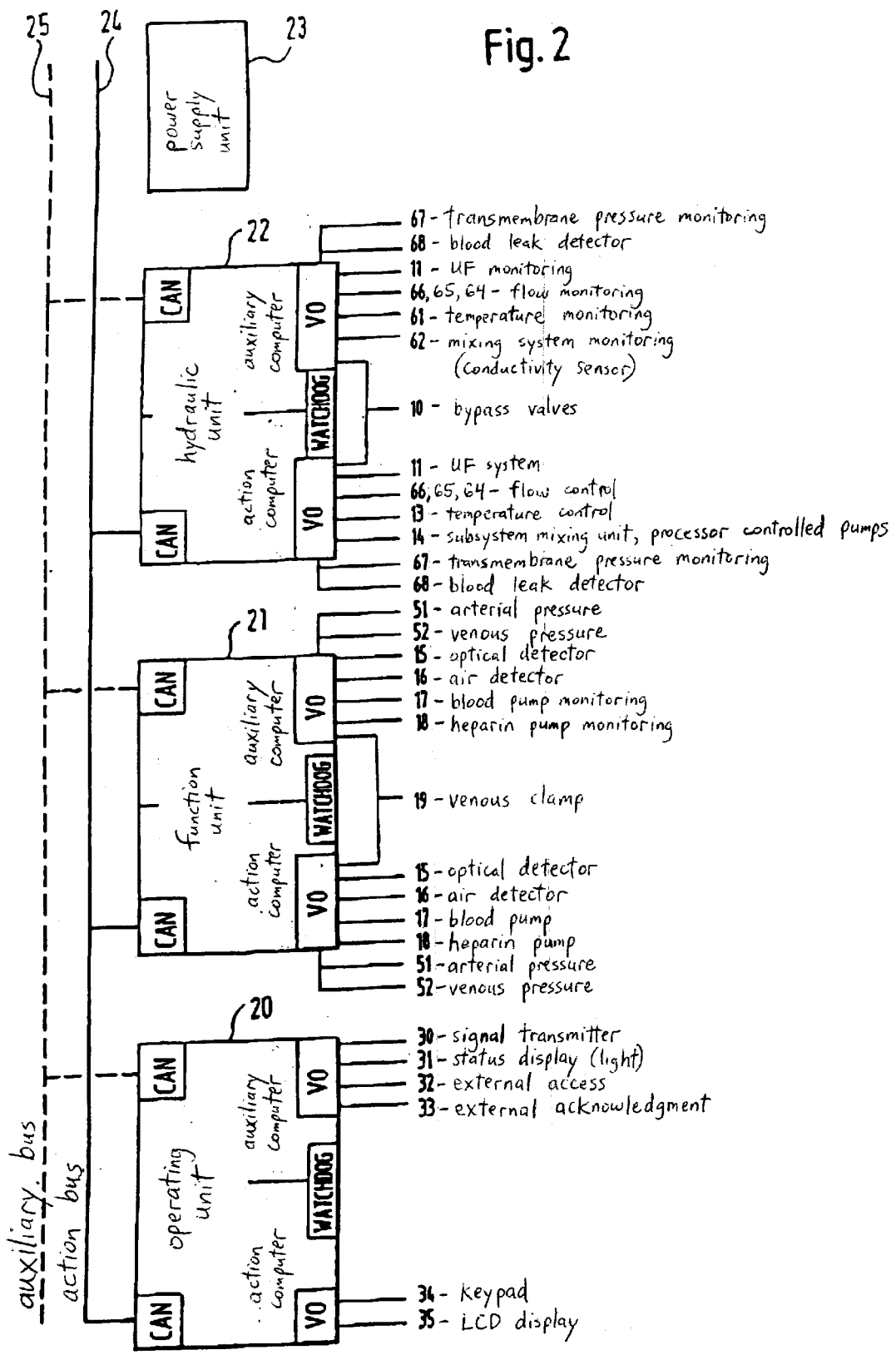

BLOOD TREATMENT MACHINE

The invention relates to a blood treatment machine with a blood treatment component, with a blood line for transporting blood between a patient and the blood treatment component and with control units for monitoring and controlling the blood transport and/or the blood treatment.

BACKGROUND OF THE INVENTION

Dialysis machines, hemofiltration machines or blood separation machines are known generally as blood treatment machines. Accordingly, dialyzers, hemofilters, plasma filters, adsorbers or blood centrifuges are used as blood treatment components of these machines.

German Patent 37 36 712 C2 describes a generic blood purifying machine. With this known blood purifying machine, various parameters (e.g., composition, temperature and throughput of the dialysis fluid) are controlled and/or regulated by various control devices or controlling elements (e.g., pumps, heaters, valves and pressure regulators) and monitored by appropriate sensors (e.g., temperature sensors, pressure sensors, air bubble sensors).

It is of crucial importance to ensure the functioning of the individual control units, because otherwise life-threatening situations for the patient may occur. To increase functional reliability, redundant computer units, each consisting of a controlling processor unit and a monitoring processor unit, are provided within a control unit, according to German Patent 37 36 712 C2. The control units communicate with one another in a star pattern by way of a main control device, with the controlling processor devices communicating with one another via a central main controlling processor device, and the monitoring processor devices communicating with one another via a central main monitoring processor device.

One disadvantage of this computer architecture of the previously known blood treatment machine, however, is that a failure of a central main processor unit can still lead to a total failure of the blood treatment machine.

SUMMARY OF THE INVENTION

The present invention is a system to further increase the functional reliability of the previously known blood treatment machines.

In one embodiment, the invention is thus a blood treatment machine comprising a blood treatment component, a blood line for transporting blood between a patient and the blood treatment component, at least two control units each having an action computer and an auxiliary computer communicating with the action computer, for monitoring and controlling the blood treatment machine, an action bus interconnecting each of the action computers and an auxiliary bus interconnecting each of the auxiliary computers. The invention also includes a table stored in at least one of the action computer or the auxiliary computer in each unit, said table assigning an error processing routine to errors selected from the group consisting of errors occurring in a control unit, errors occurring due to action bus communications or auxiliary bus communications, and error messages received by a control unit. At least one of the action computer and the auxiliary computer is adapted to send an error message to the respective bus as directed by the error processing routine.

The method of the present invention achieves the goal of greater reliability because, unlike a blood treatment machine of the generic type where the action computers are linked together by an action bus and the auxiliary computers are linked together by an auxiliary bus, communication between the action computer and the auxiliary computer is provided by a minimum of two control units.

A table is stored by the action computer and/or by the auxiliary computer in each of the minimum of two control units. In these tables, error cases occurring on the respective control unit and/or due to the bus communication and error messages received by the respective control unit, are assigned to an error processing routine. The action computer and/or the auxiliary computer of a control unit then places an error message on the respective bus as soon as the error processing routine provides for it.

Because of the direct communication connection between the action computer and the auxiliary computer within one control unit, decentralized communication is possible between the individual control units, without failure of an individual control unit leading to failure of the entire blood treatment machine. Depending on the type of communication, the action bus and/or the auxiliary bus may be used, depending on whether the transmitting unit is an action computer or an auxiliary computer.

In contrast with the hierarchical communication system known from German Patent 37 36 712 C2, independent error processing is possible with the invention. According to German Patent 37 36 712 C2, it is assumed that an error message must first be sent to a main controlling processor device or to a main monitoring processor device, and these devices then decide which functions the subordinate units must execute on the basis of the error case. In contrast with that, a table which already contains corresponding error processing routines for the control unit is stored on each control unit according to this invention. With regard to entries in the table, a distinction must be made between error sources occurring on the respective control unit and error messages received by the control unit from the outside over the action bus and/or the auxiliary bus. Error cases can be ascertained by the action computer as well as the auxiliary computer. The error table of one control unit is expediently stored on the action computer as well as on the auxiliary computer.

The blood treatment machine according to the present invention thus includes control units which can be run independently and do not need a higher-level supervisory computer when error sources occur. In this way, each control unit is intrinsically a safe, and can guarantee the security of the task assigned to it.

According to a preferred embodiment, the action computer and the auxiliary computer are each connected to a control unit with measuring sensors and/or controlling elements and measuring sensors. According to another preferred embodiment, the action computer and the auxiliary computer of one control unit for monitoring and controlling components vital to the patient are each connected in parallel to measuring sensors and controlling elements.

According to yet another preferred embodiment of the invention, in safety-critical cases the error processing routine may provide for the respective control unit to be switched to a safe status for the blood treatment independently by their controlling elements which are addressed by the control computer and/or the auxiliary computer.

Although a redundant control approach is pursued for vital components, control of subordinate components may be limited to control by an action computer or an auxiliary computer operating independently. In this way, the available computing power can be utilized optimally without having to curtail the safety of the system.

According to another preferred embodiment, an alarm is triggered in monitoring vital components of the blood treatment machine when the action computer and the auxiliary computer supply different results. Then the blood treatment machine is shut down in such a manner that life-threatening situations for the patient can always be ruled out.

When the blood treatment machine is a dialysis machine, an operating unit, a hydraulic unit and a function unit are preferably provided as control units. The hydraulic unit and the function unit control and monitor vital components of the blood treatment machine, so that the sensors and actuators connected to it are controlled and analyzed by the action computer and the auxiliary computer. For example, a display screen and a keyboard are connected to the action computer of the operating unit, and a status display and an external interface are connected to the auxiliary computer of the operating unit.

The hydraulic unit preferably includes at least one device for processing dialysis fluid, and one for balancing and ultrafiltration, while the function unit includes at least an optical detector, an air detector, an arterial and venous pressure sensor, a blood pump, a heparin pump and a venous clamp.

BRIEF SUMMARY OF THE DRAWINGS

Additional details and advantages of this invention are explained in greater detail on the basis of an embodiment in the form of a dialysis machine shown in the drawings. In the drawings:

FIG. 2: is a block diagram of the control units for the dialysis machine according to FIG. 1.

DETAILED DESCRIPTION OF THE INVENTION

Figure 1:
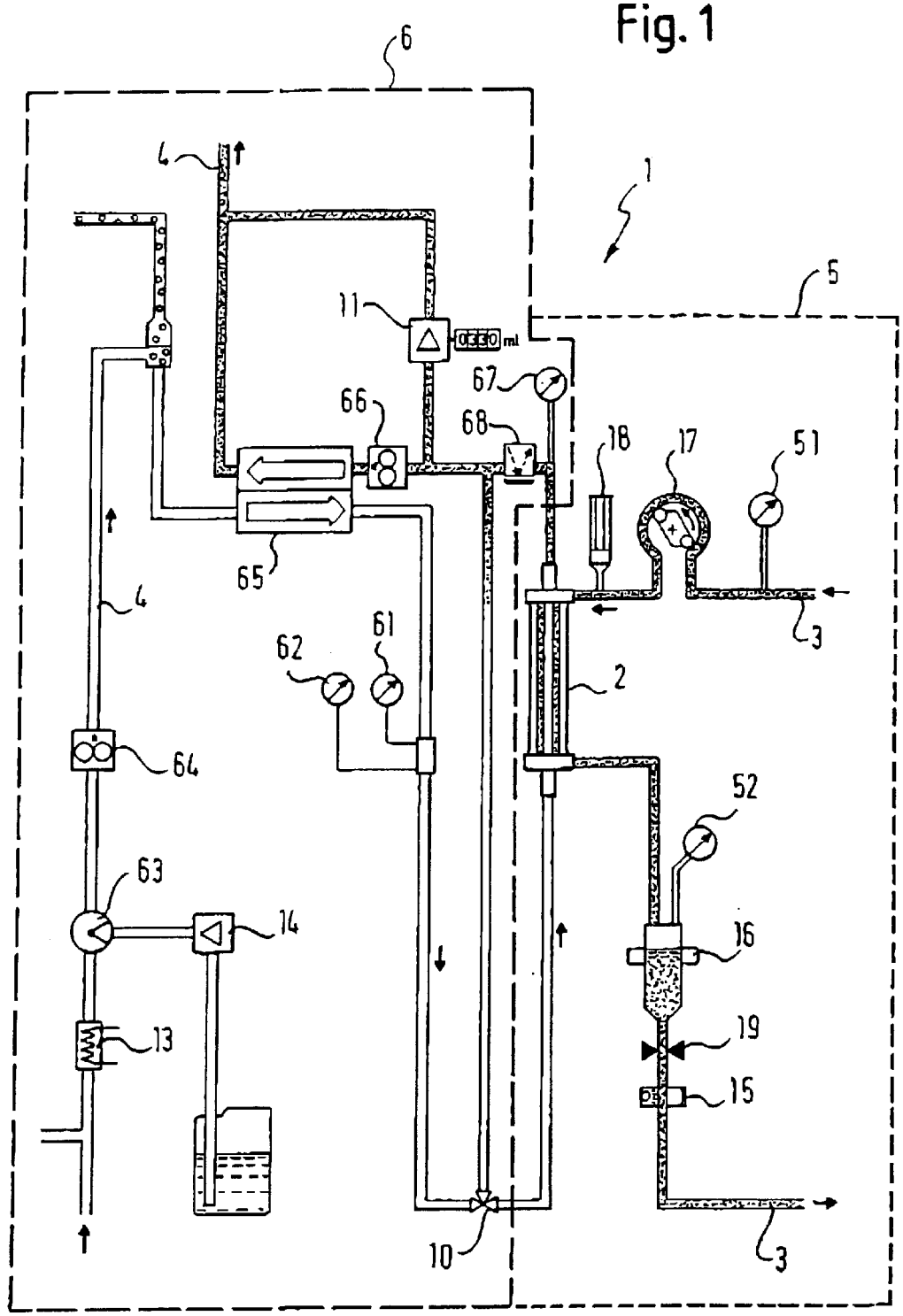
FIG. 1: is a schematic diagram showing the components of a dialysis machine.

FIG. 1 shows a schematic diagram of the components of a dialysis machine. Dialysis machine 1 has a membrane filter 2 which is connected to a blood line 3 for conveying blood between a patient and the dialyzer. A cleaning circuit 4 is connected to two other connections of membrane filter 2. In this circuit, dialysis fluid is sent to membrane filter 2 where it absorbs toxic substances that are removed from the blood.

Consequently, dialysis machine 1 can be subdivided into blood system 5 and hydraulic system 6, with blood system 5 being controlled by function unit 21 and hydraulic system 6 being controlled by hydraulic unit 22.

In its basic design, blood system 5 includes a blood pump 17, a heparin pump 18, an air detector 16, a venous clamp 19, an optical detector 15 and an arterial and a venous pressure sensor 51, 52. Basic components of hydraulic system 6 include UF pump 11, bypass valve 10, heater 13, mixing system 14, degassing pump 64, balancing unit 65, dialysis fluid pump 66 of transmembrane pressure monitor 67 and blood leak detector 68.

During operation, the water supplied is heated by heater 13 upstream from mixing point 63. The concentration pump 14 mixes the dialysis fluid concentrate with water in a preset ratio selected by the operator. Degassing pump 64 is also controlled in such a way that only degassed fluids circulate in circuit 4. In balancing chamber 65, the flow of dialysate to and from dialyzer 2 is balanced to be symmetrical, and a precise quantity of ultrafiltrate is removed by removing the desired quantity by controlling UF pump 11. The desired flow rate in circuit 4 is achieved by dialysis fluid pump 66 and a coordinated interaction of the inlet and outlet valves, not shown in the drawings, of the two balancing chambers of balancing unit 65 connected in parallel. The transmembrane pressure is monitored with UF pressure sensor 67. Finally, a blood leak in dialyzer 2 can be detected with blood leak detector 68.

FIG. 2 shows a block diagram of the control units for the dialysis machine according to FIG. 1. The control units provided include an operating unit 20, a function unit 21 and a hydraulic unit 22. The individual control units each consist of an action computer and an auxiliary computer.

All the control units receive electric power from a power supply unit 23, and the power supply unit 23, in turn, preferably has redundant components to prevent failure of the entire dialysis machine when there is a failure of one power supply unit.

The action computers of each control unit are interconnected by an action bus 24, and the auxiliary computers are interconnected by an auxiliary bus 25. For communication between action computers of various control units, an addressed communication is applied to the action bus by the transmitting action computer, and is routed to the respective action computer serving as the recipient on the basis of the address. In addition, communication within each control unit is possible between an action computer and an auxiliary computer, so that messages can also be sent from one action computer of a control unit to an auxiliary computer of another control unit. Conversely, messages can be sent from an auxiliary computer of one control unit to an action computer of another control unit.

In addition to actively sending messages from one control unit to another control unit, it is also possible for certain information to be requested from other control units. Receipt of the requested information is controlled by the timing in a conventional manner. If the information fails to arrive, additional actions must be taken by the respective control unit, such as termination of the communication with the respective control unit and sending a message to another control unit. The loss of one control unit does not necessarily lead to failure of the entire dialysis machine, because the other control units can continue to communicate with one another.

The measurement and control elements of the hydraulic unit and the function unit can be connected in parallel to the respective action computer and auxiliary computer or they may be provided in a redundant design. A signal transmitter 30, a status display 31, an external access 32 and an external acknowledgment 33 are connected to the auxiliary computer of the operating unit. A keypad 34 and an LCD display 35 are connected to the action computer of the operating unit 20.

Error processing according to this invention is explained on the basis of the following example. The settings for the mixing system 14 are set by the operator on operating unit 20, and the corresponding entries made on keypad 34 are analyzed by the action computer of the operating unit 20. An acknowledgment to the operator is provided by LCD display 35. The new set point values are relayed over the action bus 24 to all the other action computers of the other control units. The action computer of the hydraulic unit 22 then calculates new setting values for the active mixing system 14 from the set point values, transmitting these values to the mixing unit 14.

The auxiliary computer of the hydraulic unit 22 executes the same computing operations as the corresponding action computers, with additional tolerance thresholds being provided. When the tolerances are exceeded, a corresponding error message is output on the basis of a deviation between the action computer and the auxiliary computer. In addition, the auxiliary computer monitors the composition of the dialysis fluid by means of conductivity sensor 62.

If an error in the mixing system is detected by the auxiliary computer of the hydraulic unit 22, e.g., because the composition of the dialysate is not within the desired limits on the basis of the measurement by the conductivity cell, the hydraulic unit immediately controls bypass valves 10 in such a way that the flow of dialysis fluid bypasses the dialyzer and the patient is protected. The alarm triggered on the basis of the conductivity monitoring is relayed via the auxiliary bus 25 to all the other auxiliary computers connected to it. Each auxiliary computer-then also initiates the required measures.

In operating unit 20, the auxiliary computer switches the status display 31 to red and delivers an alarm signal over signal transmitter 30. The alarm is also relayed to the action computer of the operating unit 20. The action computer of the operating unit 20 in turn displays for the operator a description of the alarm on the LCD display 35. The action computer and the auxiliary computer of function unit 21 then each decide which consequences are to be inferred from the alarm status. In the present case, circulation of blood in the extra corporeal circuit is maintained for a period of time. If no entries are made on the operating unit after a certain period of time, for example after 10 minutes, the blood pump is stopped and the venous clamp is closed.

It will be apparent to those skilled in the art that various modifications and variations can be made in the structure and methodology of the present invention, without departing from the spirit or scope of the invention. Thus, it is intended that the present invention covers the modifications and variations of this invention provided they come within the scope of the appended claims and their equivalents.

What is claimed is:

1. A blood treatment machine comprising:
    a blood treatment component;
    a blood line for transporting blood between a patient and the blood treatment component;
    at least two control units, each control unit having an action computer and an auxiliary computer communicating with the action computer, for monitoring and controlling the blood treatment machine;
    an action bus interconnecting each of the action computers;
    an auxiliary bus interconnecting each of the auxiliary computers; and
    a table stored in at least one of the action computer or the auxiliary computer in each unit, said table assigning an error processing routine to errors selected from the group consisting of errors occurring in a control unit, errors occurring due to action bus communications or auxiliary bus communications, and error messages received by a control unit;
    wherein at least one of the action computer and the auxiliary computer is adapted to send an error message to the respective bus as soon as the error processing routine provides for the error message to be sent.

2. The blood treatment machine according to claim 1, further comprising a measuring element and a controlling element connected to at least one of the action computer and the auxiliary computer.

3. The blood treatment machine according to claim 2, wherein the action computer and the auxiliary computer of one of the at least two control units are connected in parallel to the measuring element and to the controlling element.

4. The blood treatment machine according to claim 3, further comprising an alarm capable of being triggered when sensing or computation of a selected parameter carried out by the action computer and the auxiliary computer are different.

5. The blood treatment machine according to claim 4, wherein the error processing routine is adapted to cause a control unit to independently place controlling elements in a condition adapted to safeguard blood processing from the errors.

6. The blood treatment machine according to claim 5, wherein the blood treatment machine is a dialysis machine, and the appropriate control units are an operating unit, a hydraulic unit and a function unit.

7. The blood treatment machine according to claim 6, further comprising a display screen and a keyboard connected to the action computer of the operating unit, and a status display and an external interface connected to the auxiliary computer of the operating unit.

8. The blood treatment machine according to claim 6, wherein the hydraulic unit further comprises a dialysis fluid processing device, a balancing unit and an ultrafiltration device.

9. The blood treatment machine according to claim 6, further comprising an optical detector, an arterial pressure sensor, a venous pressure sensor, an air detector, a blood pump, a heparin pump and a venous clamp connected to the function unit.

* * * * *